US009579532B2

(12) United States Patent
Hassan et al.

(10) Patent No.: US 9,579,532 B2
(45) Date of Patent: Feb. 28, 2017

(54) BREACH OR CONTAMINATION INDICATING ARTICLE

(71) Applicant: Ansell Limited, Richmond, Victoria (AU)

(72) Inventors: Noorman Bin Abu Hassan, Shah Alam (MY); Michael S. Zedalis, Mendham, NJ (US); Dave Narasimhan, Flemington, NJ (US)

(73) Assignee: Ansell Limited, Victoria (AU)

( * ) Notice: Subject to any disclaimer, the term of this patent is extended or adjusted under 35 U.S.C. 154(b) by 366 days.

(21) Appl. No.: 14/204,513

(22) Filed: Mar. 11, 2014

(65) Prior Publication Data
US 2014/0259332 A1    Sep. 18, 2014

Related U.S. Application Data

(60) Provisional application No. 61/777,307, filed on Mar. 12, 2013.

(51) Int. Cl.
*B32B 33/00* (2006.01)
*G01N 21/75* (2006.01)
(Continued)

(52) U.S. Cl.
CPC .............. *A62D 5/00* (2013.01); *G01N 21/77* (2013.01); *G01N 21/78* (2013.01); *G01N 21/94* (2013.01);
(Continued)

(58) Field of Classification Search
CPC .............. A62D 5/00; Y10T 428/31551; Y10T 428/31826; Y10T 428/31931; Y10T 156/10; G01N 21/78; G01N 31/22; B32B 33/00
See application file for complete search history.

(56) References Cited

U.S. PATENT DOCUMENTS

| 3,947,571 A | 3/1976 | Murphy et al. |
| 4,093,137 A | 6/1978 | Briar et al. |

(Continued)

FOREIGN PATENT DOCUMENTS

| CN | 1352593 A | 6/2002 |
| CN | 1437641 A | 8/2003 |
| EP | 1757931 A1 | 2/2007 |

OTHER PUBLICATIONS

Tarcha, "Polymers for controlled drug delivery", CRC Press, pp. 39-67, 1991.

(Continued)

*Primary Examiner* — Jennifer Wecker
(74) *Attorney, Agent, or Firm* — Moser Taboada

(57) ABSTRACT

Provided among other things is a breach or contamination indicating elastomeric article for indicating a breach or contamination by a selected chemical or group of chemicals, the article having an exterior and interior and comprising: (a) an interior elastomeric layer selected to resist permeation by the selected chemical(s), which interior layer is colored; and (b) a contiguous or dis-contiguous indicating layer comprising solid particles of hydrophobic dye effective to provide enhanced color on contacting hexane, cyclohexane, xylene, ethyl ether, butyl acetate, MIBK, methanol, acetonitrile and acetic acid; wherein the distribution of the indicating layer provides for a visually noticeable color change against the background of the colored interior elastomeric layer upon a breach or contamination event by a selected chemical.

26 Claims, 2 Drawing Sheets

(51) Int. Cl.
*G01N 21/78* (2006.01)
*B05D 1/18* (2006.01)
*A62D 5/00* (2006.01)
*G01N 21/94* (2006.01)
*G01N 21/77* (2006.01)
*A62B 17/00* (2006.01)
*A41D 19/00* (2006.01)
*G01N 31/22* (2006.01)

(52) U.S. Cl.
CPC .............. *B32B 33/00* (2013.01); *G01N 31/22* (2013.01); *G01N 2021/755* (2013.01); *Y10T 156/10* (2015.01); *Y10T 428/31551* (2015.04); *Y10T 428/31826* (2015.04); *Y10T 428/31931* (2015.04)

(56) References Cited

U.S. PATENT DOCUMENTS

| | | |
|---|---|---|
| 4,356,149 A | 10/1982 | Kitajima et al. |
| 4,843,014 A | 6/1989 | Cukier |
| 5,066,436 A | 11/1991 | Komen et al. |
| 5,133,087 A | 7/1992 | Machida et al. |
| 5,224,221 A | 7/1993 | Richardson et al. |
| 5,254,473 A | 10/1993 | Patel |
| 5,411,034 A | 5/1995 | Beck et al. |
| 5,459,879 A | 10/1995 | Fuchs |
| 5,549,924 A | 8/1996 | Shlenker et al. |
| 5,570,475 A | 11/1996 | Nile et al. |
| 5,650,329 A | 7/1997 | Warner |
| 5,976,881 A | 11/1999 | Klingner |
| 6,060,152 A | 5/2000 | Murchie |
| 6,060,986 A | 5/2000 | Lederer |
| 6,175,962 B1 | 1/2001 | Michelson |
| 6,358,160 B1 | 3/2002 | Winskowicz |
| 6,391,409 B1 | 5/2002 | Yeh et al. |
| 6,559,351 B1 | 5/2003 | Eakin |
| 6,709,725 B1 | 3/2004 | Lai et al. |
| 7,033,839 B1 | 4/2006 | Dobler et al. |
| 7,048,884 B2 | 5/2006 | Woodford et al. |
| 7,378,043 B2 | 5/2008 | Hassan et al. |
| 7,803,438 B2 | 9/2010 | Flather et al. |
| 8,187,534 B2 | 5/2012 | Mao |
| 2002/0091347 A1 | 7/2002 | Eakin |
| 2006/0026737 A1 | 2/2006 | Chen |
| 2006/0059603 A1 | 3/2006 | Peng et al. |
| 2006/0068140 A1* | 3/2006 | Flather ............... A41D 19/0065 428/36.1 |
| 2007/0048876 A1 | 3/2007 | Flor et al. |
| 2008/0108142 A1 | 5/2008 | Hall et al. |
| 2011/0287553 A1* | 11/2011 | Hassan .................. B32B 33/00 436/164 |
| 2012/0266355 A1* | 10/2012 | Husain ............... A41D 19/0027 2/159 |

OTHER PUBLICATIONS

"Chemical Resistance Guide Permeation & Degradation Data", Ansell, 8 Pages, 2008.
International Search Report, Mar. 16, 2012 for PCT Application No. PCT/US2011/048589, 10 Pages.
Chinese Office Action dated Aug. 30, 2016 for Application No. 201480014448.7.
Supplementary European Search Report for application No. EP 14764503.0 dated Oct. 24, 2016, 15 pgs.

* cited by examiner

BREACH OR CONTAMINATION INDICATING ARTICLE

CROSS-REFERENCE TO RELATED APPLICATION

This application claims benefit of U.S. Provisional Patent Application Ser. No. 61/777,307, filed Mar. 12, 2013, which is referenced herein in its entirety.

BACKGROUND

The present application relates generally to protective articles such as gloves, other wearable items and other protective flexible barriers that provide an indication of a chemical and/or mechanical breach of the article's protective surface.

Many workers come into contact with hazardous or pathogenic materials for which protection is desired. For example, industrial workers often come in contact with hazardous chemicals, including organic solvents, acids and bases. While permeation rates are known for various latex material protective compositions under laboratory testing conditions, a worker may not know when there is a chemical permeation occurring within the protective article during actual use—especially since failure of the protective wear depends on the amount, concentration or type of the contacted chemical and the thickness of the protective product.

It is known in the art that various types of articles can be used to protect individuals from these various hazardous materials. For example, gloves can be provided which protect an individual's hands and/or arms, and condoms can be provided which protect an individual's genitalia and body cavities. Such articles, however, can be compromised due to, for example, chemical permeation, punctures, partial thickness cuts, and the like. Protective articles that provide an indication that an actual breach of this type has occurred will allow the user to remove the article to limit or prevent exposure.

Hassan et al., US Pat. Application 2011/0287553, describes articles with indicator for indicating contamination or breach with microcapsules containing a dye, typically in a hydrophobic material. The microcapsules are believed to give a broad range of sensitivity to contaminating or breaching solvent. It has now been recognized that the range of sensitivity can be expanded, while simplifying the production of the articles.

There is a continuing need in the art for improved indicating articles which protect users from hazardous materials.

SUMMARY

Provided for example is a breach or contamination indicating elastomeric article for indicating a breach or contamination by a selected chemical or group of chemicals, the article having an exterior and interior and comprising: (a) an interior elastomeric layer selected to resist permeation by the selected chemical(s), which interior layer is colored; and (b) a contiguous or dis-contiguous indicating layer comprising solid particles of hydrophobic dye effective to provide enhanced color on contacting hexane, cyclohexane, xylene, ethyl ether, butyl acetate, methyl isobutyl ketone (MIBK), methanol, acetonitrile and acetic acid; wherein the distribution of the indicating layer provides for a visually noticeable color change against the background of the colored interior elastomeric layer upon a breach or contamination event by a selected chemical.

Further provided, for example, is a combination of a chemical protective article formed of laminated LCP multilayer film and the breach or contamination indicating elastomeric article described herein, shaped and sized to fit to the interior of the laminated LCP multilayer film article.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

Figure 1:
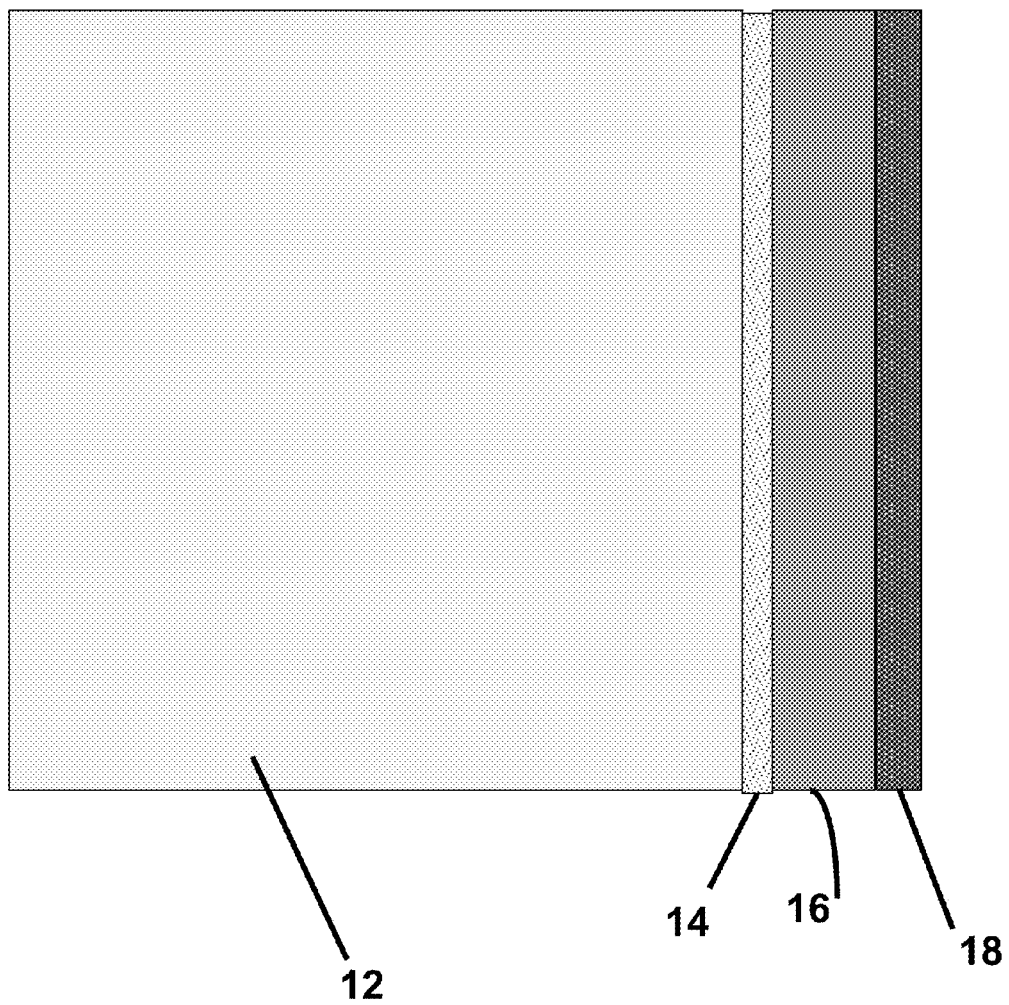
FIG. 1 depicts a cross-section of an article according to the invention.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

As one of skill in the art will recognize, the point of breach of an industrial glove is generally reached upon solvent exposure near the protective (e.g., outer) layer's permeation breakthrough time, which is generally dependent on the protective layer's thickness and degree of chemical resistance. However, estimations of breakthrough time measured on unflexed gloves may be unreliable because flexing is known to affect breakthrough time. The use of an indicating layer overcomes this problem since a breach of the glove can be immediately detected, whether in the flexed or unflexed state. Real breakthrough may not match the analytical breakthrough time measured for example as per EN 374-3 (European Standards) testing.

In one embodiment article of the invention, as illustrated in FIG. 1, there is an exterior elastomeric layer 12, an indicating layer 14 and an interior elastomeric layer 16. In the indicating layer are solid particles of hydrophobic indicator dye illustrated by dots. There can be a further interior layer(s) 18 adapted to provide comfort to the wearer. Such a layer 18 can be for example a polyurethane layer that stabilizes flock for the comfort of a hand, foot or the like.

The exterior elastomeric layer 12 is adapted to be sufficiently translucent that the appearance of color at or about the indicating layer 14 can be seen from the exterior of the article—such as by the user of the article. The interior elastomeric layer 16 is adapted to be colored preferably with a dye that is resistant to the solvents for which the article is rated as protective wear. In embodiments, the dye can be resistant to solubilization by selected chemicals, or the elastomeric layer may otherwise inhibit migration of the dye. The color of the interior elastomeric layer 16 is selected to serve as a backdrop that highlights the appearance of color at or about the indicating layer. For example, the interior elastomeric layer 16 can be green, and the hydrophobic indicator dye can be red. Or, for example, interior elastomeric layer 16 can be blue, and the hydrophobic indicator dye can be red or yellow. An opaque white can be used as background color for a broad array of indicator dyes. (By "opaque" it is meant that the dye as formulated in the layer is sufficiently opaque as to provide a background that accentuates detection of solubilized dye from the indicating layer.

The dye is selected to be one that as solid particles (e.g., dye precipitate, dye crystals) is sufficiently concentrated so that an amount that is effective in producing color when solubilized but does not, in the solid form (e.g., dispersed, isolated particles), have a notable color effect against the backdrop. An amount of the solid form that does not have notable color effect is provided in the indicating layer 14. But, that amount is also sufficient to provide a notable color effect against the backdrop when solubilized.

Those of skill will recognize that additional layers may be present in the embodiment of FIG. 1. For example additional layers may intervene between exterior elastomeric layer 12 and indicating layer 14, or between indicating layer 14 and interior elastomeric layer 16, so long as such layers do not interfere with the color background function of interior elastomeric layer 16. Similarly, there may be additional interior or exterior layers. As noted elsewhere, exterior layer 12 can be absent (e.g., splash indicating article).

It has been unexpectedly discovered that a dye that is sufficiently hydrophobic to remain concentrated (and thus not substantially colored) in the indicating layer during aqueous latex dip processing to form the interior elastomeric layer is nonetheless sensitive to a broad range of potential infiltrating solvents. Accordingly, the dye has limited solubility in water.

Dyes can be selected empirically based on dip processing tolerance and ability to detect the following solvent infiltrations, save water:

TABLE

| | Polarity Index | Permeation Rating | Dielectric Constant (20° C.) |
|---|---|---|---|
| Hexane | 0.1 | E | 1.89 |
| Cyclohexane | 0.2 | G-E | 2.023 |
| Xylene | 2.5 | E | 2.27 (para-xylene) |
| Ethyl Ether | 2.8 | E | 4.335 |
| Butyl Acetate | 4.0 | F | |
| Methyl Isobutyl Ketone (MIBK) | 4.2 | P | |
| Methanol | 5.1 | E | 32.63 (25°) |
| Acetonitrile | 5.8 | F | 37.5 |
| Acetic Acid | 6.2 | G | 6.15 |
| Water | 10.2 | E | 78.54 |

(0 = Highly Non-Polar)
(10 = Highly Non-Polar)

The above solvents, less water (nine solvents), are deemed the "representative solvents."

In the above, the polarity index is a proprietary, but well recognized in the chemical arts, rating system that provides a relative measure of the degree of interaction of the solvent with various polar test solutes; and the permeation rating is a relative rating of E—excellent, G—good, F—fair, P—poor and NR—not recommended as obtained with Solvex 37-165 nitrile gloves from Ansell (Iselin, N.J.). The permeation rating standard is:

TABLE

E—excellent protection; permeation rate of <0.9 ug/cm^2/min
VG—very good; permeation rate of <9 ug/cm^2/min
G—good protection; permeation rate of <90 ug/cm^2/min
F—fair protection; permeation rate of <900 ug/cm^2/min
P—poor protection; permeation rate of <9000 ug/cm^2/min
NR—not recommended; permeation rate of >9000 ug/cm^2/min Appropriate hydrophobic dyes, such as Solvent Red 26 (atomic formula C25H22N4O; scientific name 1-[[2,5-dimethyl-4-[(2-methylphenyl)azo]-phenyl]azo]-2-naphthol; C.I. 26120; AKA Oil Red EGN), while expected to dissolve and give color well in hexane, have been found to provide indicator with all of the above solvents except water. Thus, it can be expected that a dye providing indicator across all of the representative solvents shall indicate against most solvents with a polarity index of about 0.1 (or less) to about 6.2 (or more), such as in a range from 0.05 to 8. For a dye effective with the representative solvents, it is further expected that for solvents that are not Brønsted-Lowry acids or bases, a dielectric constant (20-25° C.) of about 1.8 to about 45 should provide that the indicator dye is effective. For a dye effective with the representative solvents, it is further expected that for solvents that are Brønsted-Lowry acids or bases, a dielectric constant (20-25° C.) of 1.8 to 12.5 should provide that the indicator dye is effective.

Testing for the above sensitivity to the representative solvents can be conducted with a material according to FIG. 1, in which the exterior layer 12 is a dipped nitrile layer, an indicating layer, a colored interior layer 16, and no further interior layer 18. The exterior layer 12 can have thickness of 14 mil (356 micrometer or mcm), or be thinner. The interior layer can be, for example, 2.5 mil (64 mcm) thick, or another thickness that provides a good background. An area of the exterior layer can then be contacted with challenge solvent for a period of time sufficient to exceed the time needed for a significant break-through with the given solvent. Separable two-part chambers with glass viewing windows, such as used in measuring liquid or vapor breakthrough times can be used.

An alternative measure of dye suitability is provided by consideration of the octanol-water Log D at pH 5.5, and the molar extinction coefficient. For Solvent Red 26, Log $D_{5.5}$ is 7.16, and the extinction coefficient in chloroform is $\geq 26{,}000$ MA^-1 cm^-1 at a visible wavelength ($\lambda_{max}$ 521 nm). (As reported at www.sigmaaldrich.com for its Oil Red EGN product.) Solvent Red 26 has the following structure:

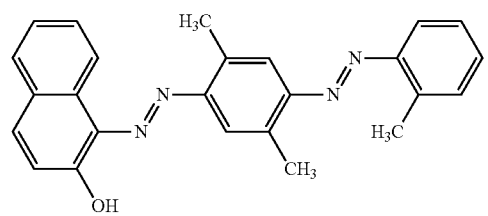 [SMILES: Cc1ccccc1/N=N/c1cc(C)c(/N=N/c2c(O)ccc3ccccc23)cc1C]

It is expected that a Log D (pH 5.5) of about 4 to about 10 can provide a wide range of solvent sensitivities. It is expected that an extinction coefficient in chloroform of greater than about 10,000 M^-1 cm^-1 can provide a useful color response against an appropriate background.

Dye particles in the indicating layer can be, on average, about 0.5 to about 4 micron, or about 0.5 to about 3 micron in size, as measured for example by light scattering. In embodiments, the average particle size is within one of the above ranges. In embodiments, 90% or more of the particles fall within one of the above ranges.

Other dyes that are anticipated to be useful, as can be confirmed as outlined herein, include without limitation:

TABLE

Oil Red O (differing from Solvent Red 26 by an additional methyl in the right phenyl, para to the first methyl)
Sudan III (differing from Solvent Red 26 by lacking all three methyls)
Sudan Red 7B (differing from Sudan III by ethyl amino in place of hydroxy)
Sudan IV (differing from Solvent Red 26 by lacking the middle methyl in the structure as illustrated above)
Oil Yellow DE (N,N-diethyl-p-(phenylazo)aniline)
Solvent Blue 35 (1,4-bis(butylamino)anthraquinone)
Solvent Yellow 124 (N-Ethyl-N-[2-[1-(2-methylpropoxy)ethoxy]ethyl]-4-phenyldiazenylaniline)

Further dyes that are anticipated to be useful, as can be confirmed as outlined herein, include without limitation the solvent dyes in the following six tables, which dyes are available from Hangzhou Sunny Chemical Corp Ltd. (Hangzhou, China; www.sunnychemical.com/):

TABLE

| Blue Dyes | | |
| --- | --- | --- |
| Solvent Blue B Base | Solvent Blue 4 | CAS#6786-83-0 |
| Solvent Blue BO Base | Solvent Blue 5 | CAS#1325-86-6 |
| Solvent Transparent Blue HB | Solvent Blue 11 | CAS#128-85-8 |
| Solvent Blue B | Solvent Blue 35 | CAS#17354-14-2 |
| Solvent Blue AP | Solvent Blue 36 | CAS#14233-37-5 |
| Solvent Fast Blue HBSN | Solvent Blue 38 | CAS#1328-51-4 |
| Solvent Transparent Blue S-RLS | Solvent Blue 45 | CAS#37299-23-5 |
| Solvent Oil Blue ZV | Solvent Blue 58 | CAS#61814-09-3 |
| Solvent Transparent Blue N | Solvent Blue 59 | CAS#6994-46-3 |
| Solvent Oil Blue GN | Solvent Blue 63 | CAS#6408-50-0 |
| Solvent Transparent Blue 2R | Solvent Blue 68 | CAS#4395-65-7 |
| Solvent Blue GL | Solvent Blue 70 | CAS#12237-24-0 |
| Solvent Blue GP | Solvent Blue 78 | CAS#2475-44-7 |
| Solvent Blue 2R | Solvent Blue 97 | CAS#61969-44-6 |
| Solvent Transparent Blue AG | Solvent Blue 101 | CAS#6737-68-4 |
| Solvent Blue 2B | Solvent Blue 104 | CAS#116-75-6 |
| Solvent Transparent Blue R | Solvent Blue 122 | CAS#67905-17-3 |
| Solvent Transparent Blue 3R | Solvent Blue 128 | |

TABLE

| Yellow Dyes | | |
| --- | --- | --- |
| Solvent Oil yellow G | Solvent Yellow 2 | CAS#60-11-7 |
| Solvent Fluorescent Yellow 8GF | Solvent Yellow 5 | CAS#85-84-7 |
| Solvent Oil Yellow R | Solvent Yellow 14 | CAS#842-07-9 |
| Solvent Oil Yellow 3G | Solvent Yellow 16 | CAS#4314-14-1 |
| Solvent Oil Yellow SG | Solvent Yellow 18 | CAS#6407-78-9 |
| Solvent Spirit Light Fast Yellow GR | Solvent Yellow 19 | CAS#10343-55-2 |
| Solvent Yellow BL | Solvent Yellow 21 | CAS#5601-29-6 |
| Solvent Oil Yellow GS | Solvent Yellow 28 | CAS#5844-01-9 |
| Solvent Yellow 4G | Solvent Yellow 33 | CAS#8003-22-3 |
| Solvent Auramine Base | Solvent Yellow 34 | CAS#492-80-8 |
| Solvent Fluorescent Yellow R | Solvent Yellow 43 | CAS#19125-99-6 |
| Solvent Oil Golden Yellow 2G | Solvent Yellow 56 | CAS#2481-94-9 |
| Solvent Transparent Yellow 2GH | Solvent Yellow 72 | CAS#61813-98-7 |
| Solvent Transparent Yellow G | Solvent Yellow 77 | CAS#2832-40-8 |
| Solvent Fast Yellow 2GL | Solvent Yellow 79 | CAS#12237-31-9 |
| Solvent Yellow KR | Solvent Yellow 82 | CAS#12227-67-7 |
| Solvent Transparent Yellow 3G | Solvent Yellow 93 | CAS#4702-90-3 |
| Solvent Fluorescent Yellow 3G | Solvent Yellow 98 | CAS#12671-74-8 |
| Solvent Yellow 3G | Solvent Yellow 114 | CAS#75216-45-4 |
| Solvent Fluorescent Yellow 9GF | Solvent Yellow 145 | CAS#27425-55-4 |
| Solvent Fluorescent Yellow 10GN | Solvent Yellow 160:1 | CAS#94945-27-4 |
| Solvent Transparent Yellow GS | Solvent Yellow 163 | CAS#13676-91-01 |
| Solvent Transparent Yellow 3GL | Solvent Yellow 176 | CAS#10319-14-9 |
| Solvent Transparent Yellow 6G | Solvent Yellow 179 | CAS#80748-21-6 |
| Solvent Fluorescent Yellow 10G | Solvent Yellow 185 | CAS#27245-55-4 |

TABLE

| Orange Dyes | | |
| --- | --- | --- |
| Solvent Oil Orange RC | Solvent Orange 2 | CAS#2646-17-5 |
| Solvent Chrysoidine Base | Solvent Orange 3 | CAS#495-45-5 |
| Solvent Oil Orange 45 | Solvent Orange 45 | CAS#13011-62-6 |
| Solvent Oil Orange KRV | Solvent Orange 54 | CAS#12237-30-8 |
| Solvent Oil Orange 3G | Solvent Orange 60 | CAS#61969-47-9 |
| Solvent Oil Orange R | Solvent Orange 62 | CAS#52256-37-8 |
| Solvent Transparent Orange 2G | Solvent Orange 63 | CAS#16294-75-0 |
| Solvent Oil Orange G | Solvent Orange 86 | CAS#81-64-1 |
| Solvent Oil Orange YR | Solvent Orange 99 | |
| Solvent Transparent Orange FR | Solvent Orange 105 | CAS#31482-56-1 |
| Solvent Transparent Orange R | Solvent Orange 107 | CAS#185766-20-5 |

TABLE

| Red Dyes | | |
| --- | --- | --- |
| Solvent Oil Red G | Solvent Red 1 | CAS#1229-55-6 |
| Solvent Fat Brown B | Solvent Red 3 | CAS#6535-42-8 |
| Solvent Oil Red GB | Solvent Red 8 | CAS#33270-70-1 |
| Solvent Transparent Scarlet H | Solvent Red 23 | CAS#85-86-9 |
| Solvent Oil Red B | Solvent Red 24 | CAS#85-83-6 |
| Solvent Transparent Red S | Solvent Red 25 | CAS#3176-79-2 |
| Solvent Oil Red TXN | Solvent Red 26 | CAS#4477-79-6 |
| Solvent Oil Red 5B | Solvent Red 27 | CAS#1320-06-5 |
| Solvent Rhodamine B Base | Solvent Red 49 | CAS#509-34-2 |

TABLE-continued

Red Dyes

| | | |
|---|---|---|
| Solvent Red 5B | Solvent Red 52 | CAS#81-39-0 |
| Solvent Transparent Red RL | Solvent Red 73 | |
| Solvent Spirit Fire Red B | Solvent Red 109 | CAS#53802-03-2 |
| Solvent Transparent Red GS | Solvent Red 111 | CAS#82-38-2 |
| Solvent Fast Fire Red G | Solvent Red 119 | CAS#12237-27-3 |
| Solvent Red 2BRN | Solvent Red 122 | CAS#12227-55-3 |
| Solvent Fast Red R | Solvent Red 124 | CAS#12239-74-6 |
| Solvent Red 2BL | Solvent Red 132 | CAS#61725-85-7 |
| Solvent Transparent Red EG | Solvent Red 135 | CAS#71902-17-5 |
| Solvent Transparent Red SB | Solvent Red 145 | CAS#66057-80-5 |
| Solvent Transparent Red FB | Solvent Red 146 | CAS#70956-30-8 |
| Solvent Transparent Red HFG | Solvent Red 149 | CAS#71902-18-6 |
| Solvent Red KLB | Solvent Red 168 | CAS#71832-19-4 |
| Solvent Transparent Red 2G | Solvent Red 169 | CAS#27354-18-3 |
| Solvent Transparent Red 3B | Solvent Red 172 | CAS#63512-13-0 |
| Solvent Transparent Red E-2G | Solvent Red 179 | CAS#89106-94-5 |
| Solvent Transparent Red 2B | Solvent Red 195 | CAS#164251-88-1 |
| Solvent Fluorescent Red BK | Solvent Red 196 | CAS#52372-36-8 |
| Solvent Fluorescent Red GK | Solvent Red 197 | CAS#52372-39-1 |
| Solvent Transparent Red CHA | Solvent Red 207 | CAS#15958-69-6 |
| Solvent Fast pink PR | Solvent Red 218 | CAS#82347-07-7 |
| Solvent Fluorescent Red 5B | Solvent Red 242 | CAS#22-75-8 |

TABLE

Violet Dyes

| | | |
|---|---|---|
| Solvent Oil Violet 5BN | Solvent Violet 8 | CAS#52080-58-7 |
| Solvent Methyl Violet 10B Base | Solvent Violet 9 | CAS#467-63-0 |
| Solvent Transparent Violet ER | Solvent Violet 11 | CAS#128-95-0 |
| Solvent Oil Violet B | Solvent Violet 13 | CAS#81-48-1 |
| Solvent Violet RS | Solvent Violet 14 | CAS#67577-84-8 |
| Solvent Transparent Violet 3B | Solvent Violet 26 | CAS#2872-48-2 |
| Solvent Violet RR | Solvent Violet 31 | CAS#70956-27-3 |
| Solvent Violet 3R | Solvent Violet 36 | CAS#61951-89-1 |
| Solvent Transparent Violet 2B | Solvent Violet 37 | CAS#61969-50-4 |
| Solvent Oil Violet 2R | Solvent Violet 56 | |
| Solvent Transparent Violet RL | Solvent Violet 59 | CAS#6408-72-6 |

TABLE

Green/Brown/Black Dyes

| | | |
|---|---|---|
| Solvent Green 5B | Solvent Green 3 | CAS#128-80-3 |
| Solvent Green S-G | Solvent Green 28 | CAS#71839-01-5 |
| Solvent Brown 2RL | Solvent Brown 43 | CAS#61116-28-7 |
| Solvent Transparent Black 4B | Solvent Black 3 | CAS#4197-25-5 |
| Solvent Oil Black BR | Solvent Black 5 | CAS#11099-03-9 |
| Solvent Oil Black NB | Solvent Black 7 | CAS#8005-02-5 |
| Solvent Black H | Solvent Black 27 | CAS#12237-22-8 |
| Solvent Black N | Solvent Black 29 | CAS#61901-87-9 |
| Solvent Black BC | Solvent Black 34 | CAS#32517-36-5 |

In embodiments of the invention, the dye is an azo dye.

In embodiments of the invention as illustrated in FIG. 1, exterior elastomeric layer is about 2 mil (51 mcm) to about 40 mil (1016 mcm), such as about 14 mil (356 mcm). In embodiments, indicating layer 14 is as thick as substantially a dispersion of solid dye particles to about 2 mil, or, in embodiments, about 0.4 mil (10 mcm) to about 2 mil, such as about 1 mil (25 mcm). Interior elastomeric layer 16 is, in embodiments, about 1 mil (25 mcm) to about 10 mil (254 mcm), such as about 2 to about 3 mil (76 mcm). In embodiments, an elastomeric polymer layer (adhered to interior elastomeric layer 16) of further interior layer 18 is about 0.4 mil to about 4 mil (102 mcm) thick, such as about 1 mil to about 2 mil. For layer 18, higher thicknesses in the range are anticipated if of foamed latex. Lower thicknesses are anticipated if an adhesive is used to bind flock.

For example, where indicating layer 14 is substantially a dispersion of solid dye particles at the referenced layer interface, it can be applied there during fabrication alone or with a salt coagulant and enough binder polymer to retain it in place. For example a binding coagulant composition such as that taught in U.S. Pat. No. 7,378,043 can be used, for example utilizing polyethylene glycol or another polymer as binder polymer. The teachings on a polymeric coagulant composition of the '043 patent are incorporated herein in their entirety. The polymeric composition of U.S. Pat. No. 7,378,043 can be used without including coagulant salt. For example, a polymeric binding formulation can be applied, and hydrophobic dye particles applied to the formulation. Thereafter, a further elastomeric layer can be formed on layer 14.

Or, the indicating layer 14 can comprise a more substantial polymeric layer. Where azo or other alkali labile dyes are used, care can be taken to apply the dye in a polymeric binder formulation that is not sufficiently alkaline to deteriorate the indicating function (assuming this is an issue). For example, the polymeric binder formulation can be a Carbobond™ high solid dispersion of acrylic polymer (Lubrizol, Wickliffe, Ohio).

The indicating layer can comprise polymer selected to have low chemical resistance to the chemical being detected. Such a polymer can be selected from a Chemical Resistance Guide, such as the one found at www.ansellpro.com/download/Ansell_8thEditionChemicalResistanceGuide.pdf, to identify polymers that have low chemical resistance to the chemical being detected. A terpolymer, which is non-cross linked, is a useful carrier polymer in the indicating layer. For example, a polyurethane terpolymer can be used. Data for polyurethane is available at k-mac-plastics.com/date%20sheets/polyurethane_chemical_resistance.htm.

Capillary action between glove layers can in embodiments assist in spreading the indicator spot beyond the site of the initial breach. This capillary effect can facilitate breach rapid breach detection, allowing the user to remove the damaged glove or other article and don a new glove or other article. Breach detection can be enhanced because of the greater area of dye spread can be more clearly visible.

Foam materials, such as open cell foam elastomers, can be used as polymer material in the indicating layer 14.

In embodiments, one or more of the elastomeric layers (12, 16) have density consistent with aqueous latex dipping (as opposed for example to a density given polymer content consistent with injection molding). In certain embodiments, the barrier layers have other properties (such as elasticity) consistent, given polymer content, with aqueous latex dipping. These densities or other properties can vary with the polymer content of the elastomeric layers.

In embodiments, one or more of the elastomeric layers are made by aqueous dipping. In embodiments, one or more of the elastomeric layers has a property that distinguishes it from a layer formed by injection molding.

In embodiments, the elastomeric layers (12, 16) are formed of natural rubber (NR), polychloroprene (CP), acrylonitrile butadiene copolymer (NBR) (such as carboxylated acrylonitrile butadiene copolymer), polyisoprene (PI), polyurethane (PU), styrene-butadiene, butyl rubber (copolymer of isobutylene with isoprene, or polymer of isobutylene), or combinations thereof. In embodiments, the elastomeric layers (12, 16) are formed of CP, NBR or combinations thereof.

In embodiments, the article is a contamination indicating article (i.e., a splash protective article), whereby the exterior elastomeric layer is notably thinner, not present, or made of a less chemically resistant polymer. For example, in embodiments there is no substantial resistant layer between the indicating layer and the outside of the article. By "no substantial resistant layer" it is meant that the permeation breakthrough time with respect to one of the selected chemicals is less than for interior elastomeric layer 16. Any embodiment that is described herein as having "no substantial resistant layer" can have this feature substituted with "no substantial resistant layer by thickness." By "no substantial resistant layer by thickness" it is meant that the thickness of any relevant non-substantial layers is about 1 mil or less, or about 0.5 mil or less. In embodiments, such a layer can be at least about 0.1 mil. Such non-substantial layers can have a polymer composition that is less resistant per mil thickness than the polymer composition of the interior elastomeric layer(s). In embodiments, a non-substantial layer can be of polyurethane or foamed polyurethane.

Figure 2:
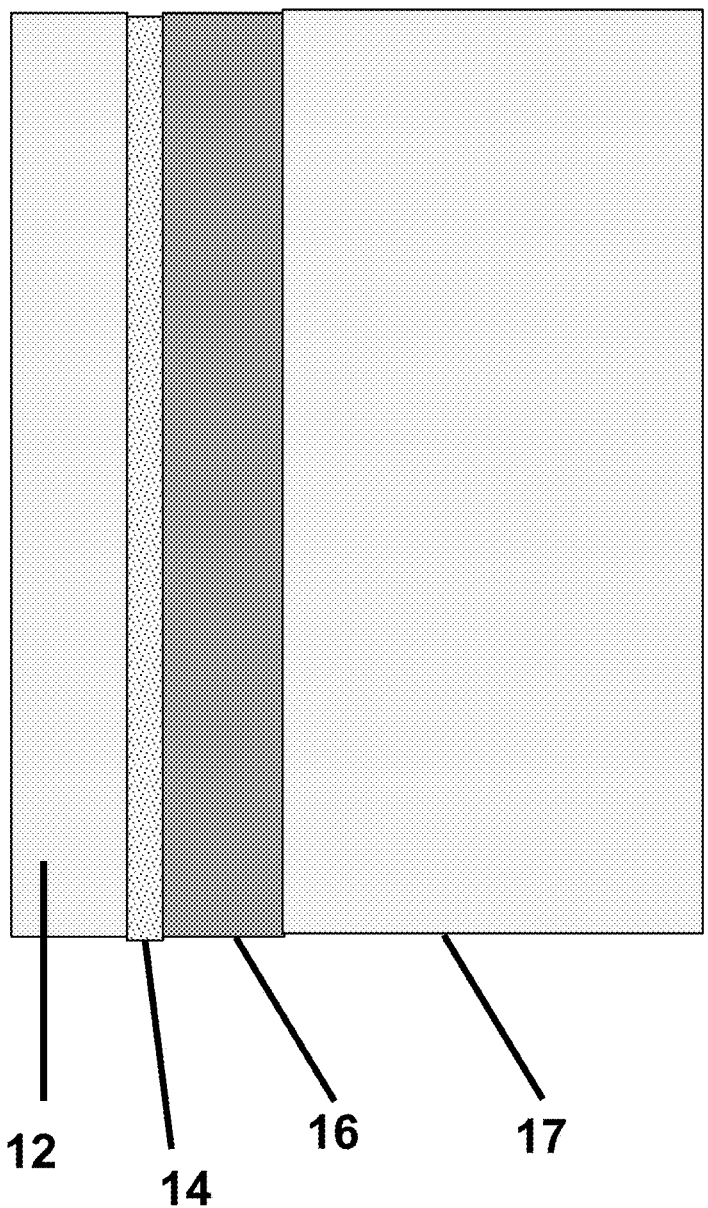
FIG. 2 shows a cross-section of another article according to the invention.

In a contamination indicating article (i.e., splash indicating article), interior elastomeric layer(s) can be thicker, such as about 2 mil (51 mcm) to about 40 mil (1016 mcm), such as about 14 mil (356 mcm). In embodiments of a contamination indicating article, there can be additional interior elastomeric layers, such as second interior elastomeric layer 17 shown in FIG. 2. As such, the thickness of colored first interior elastomeric layer 16 can be, in embodiments, about 1 mil (25 mcm) to about 10 mil (254 mcm), such as about 2 to about 3 mil (76 mcm). The exterior elastomeric layer can be in embodiments for example about 0.1 mil (2.5 mcm) to about 3 mil. As discussed in reference to FIG. 1, there can be additional layers, so long as they do not interfere with the indicating function. As noted elsewhere, exterior layer 12 can be absent from FIG. 2.

In embodiments, the first interior elastomeric layer 16 is colored with Hydrotint Green 768E (DVM Pigments & Additives Ltd., Chorley, UK) (a mixture of Pigment Green 7 (AKA, Phthalocyanine Green G; [1,2,3,4,8,9,10,11,15,16, 17,18,22,23,24,25-Hexadecachloro-29H,31H-phthalocyaninato(2-)-κ2N29,N31]copper) and Pigment White 6 (titanium dioxide)). In embodiments, the elastomer of interior elastomeric layer 16 is loaded with a diffusion-inhibiting filler(s) such as bentonite clay, modified bentonite clay, other diffusion resistant materials such as waxes, or the like. In embodiments, a blue background is provided in the interior elastomeric layer. The interior elastomer layer 16 can be colored with pigment. Pigments, by definition, are insoluble in the vehicle or substrate in which incorporated. In this case, particularly useful pigments are insoluble in water.

Other pigments can be used. For example, Phthalocyanine Blue BN (CAS #147-14-8) or Pigment Green 36 can be used.

The interior of the glove can be treated to facilitate donning, manage moisture, or both. For example, the skin-contacting inner surface can be chlorinated, foamed, flocked, a combination thereof, or the like. A further interior layer 18 or 17 can comprise a silicone emulsion or a polymer coating. A further interior layer 18 or 17 can comprise a foamed or non-foamed adhesively-bonded cotton or rayon flock, or other fabric.

For use in the current invention, the indicating layer can be applied to an exterior elastomeric layer 12, for example of the type formed in dip coating methods. In the dip-coating process, the exterior elastomeric layer can be positioned on the former in an apparent interior orientation that will be inverted prior to use of the article. Or the interior elastomeric layer can be formed first, such that no net inversion is needed.

The indicating layer can be uniformly applied to the elastomeric layer, or applied in discontinuous sections—so long as the density of segments located for breach or contamination indication is sufficient to provide the needed indicating color. For example, all or most of the palm-side surface of a glove, in the area of the palm and the fingers, can have indicating layer, while the dorsal side can have indicating layer in representative regions. Alternatively, for example, all of the area of the glove to the hand side of the wrist can have indicating layer.

In dip-coating methods it is anticipated that the solid particles of dye will be exposed to water, but shall resist solubilization. When contacted with latex that prior to dipping was alkali-stabilized, and when using alkali-sensitive dyes, it is anticipated that the use of latex coagulants or polymer binders with the dye will limit the exposure of the solid dye particles to alkali.

A surface treatment, such as chlorination, siliconization, or a polymer coating can be applied to the article to reduce any inherent tackiness. A polymer coating process for example laminates the surface of the glove with a thin layer of synthetic polymer, normally up to several micrometers in thickness, having a low-friction coefficient value to provide anti-tack and good slip properties, as disclosed in Lai et al., U.S. Pat. No. 6,709,725, which discloses a natural or synthetic rubber elastomeric article having a coating layer containing a blend of a film-forming polymer and a wax. A further exterior layer (not shown) can serve to modify the surface tack that would apply with the polymer of exterior layer 12, and can provide a substrate for an anti-tack treatment.

The manufacturing process of an indicating glove can have the following steps. a former, for example in the shape of a human hand, is (if needed to coagulate a given polymer) first dipped in a coagulant such as calcium nitrate and then is dipped in an aqueous latex emulsion of a polymer, such as a chemically resistant polymer, to form the exterior elastomeric layer. A Chemical Resistance Guide, such as one found at www.ansellpro.com/download/Ansell_8thEditionChemicalResistanceGuide.pdf, which details protection capability of various polymers and provides data on chemical permeation rates and is incorporated by reference, can be used to make polymer selections. The thickness of the exterior elastomeric layer of the glove can be built up by several dips with or without additional use of coagulant. The former at this stage has a coagulated elastomeric layer, which can next be dipped into an indicator layer composition, or otherwise have the composition applied.

Thereafter, for example, if needed to coagulate a given polymer, the former is further dipped in a latex coagulant such as calcium nitrate and then is dipped in an aqueous latex emulsion of a polymer, to form the interior elastomeric layer. Multiple dips, with or without intervening coagulant dips, can be used to build up thickness.

Alternatively, a dip process can begin with an interior layer. For example, a former, such as in the shape of a human hand, is (if needed to coagulate a given polymer) first dipped in a coagulant such as calcium nitrate and then is dipped in an aqueous latex emulsion of a polymer, such as a chemically resistant polymer, to form the interior elastomeric layer. The thickness of the interior elastomeric layer of the glove can be built up by several dips with or without additional use of coagulant. The former at this stage has a coagulated elastomeric layer, which can next be dipped into an indicator layer composition, or otherwise have the composition applied.

Thereafter, for example, if needed to coagulate a given polymer, the former is further dipped in a latex coagulant such as calcium nitrate and then is dipped in an aqueous latex emulsion of a polymer, to form the exterior elastomeric layer. Multiple dips, with or without intervening coagulant dips, can be used to build up thickness.

In an exterior first or interior first process, the indicator can be applied by just spraying or dusting fine particles of the dye, or spraying or dusting onto a binder polymer (e.g., tacky prior to curing).

In the green interior elastomeric layer embodiment, the elastomeric article will look green, with the under layer of green nitrile latex (or other colored latex) visible through the transparent or translucent latex layer. When the solvent permeates through the outer translucent nitrile layer due to latex swelling, or otherwise, the solvent dissolves the red dye, making it visible against the green background, showing a red indication. With solvent permeation, the transparent or translucent latex will swell and become somewhat opaque (milky) looking. Nonetheless, the color indication of the invention is strong enough to provide a signal visible through the swollen latex.

In embodiments, the breach or contamination indicating glove is used in conjunction with a laminated LCP (liquid crystal polymer) multilayer film, such as the film of the Barrier 2-100 (5 layers) sold by Ansell Ltd. (Richmond, AU). An above-described article of the invention is worn on the interior of an article of laminated LCP multilayer film. In embodiments, the above-described article of the invention is bonded to the laminated LCP multilayer film, such as by adhesive layer or by thermal bonding. Thermal bonding can be conducted through the above-described article to minimize any compromise to the laminated LCP multilayer film. A process utilizing a non-tacky, thermoplastic adhesive layer between the laminated LCP multilayer film and the above-described article, whereby infrared light is used to fuse the adhesive after inflating the elastomeric above-described article, can be used. Such a process is as described in U.S. Pat. No. 7,803,438, which description is incorporated herein in its entirety. Inflating the interior article assures good contact between the two articles when adhered.

In this fashion, the contamination indicating function can be used with the broad chemical resistance of laminated LCP multilayer film.

The articles that can incorporate the indicating feature of the invention include gloves, other protective wear such as aprons, chemical hazard suits (or parts thereof such as pants, jackets, sleeve guards, head coverings, or the like), non-clothing flexible shields or dams, and the like. All such articles can have breach indicating or contamination/splash indicating.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more.

The invention further includes the following embodiments:

A. A breach or contamination indicating elastomeric article for indicating a breach or contamination by a selected chemical or group of chemicals, the article having an exterior and interior and comprising: (a) an interior elastomeric layer selected to resist permeation by the selected chemical(s), which interior layer is colored; and (b) a contiguous or dis-contiguous indicating layer comprising solid particles of hydrophobic dye effective to provide enhanced color on contacting hexane, cyclohexane, xylene, ethyl ether, butyl acetate, MIBK, methanol, acetonitrile and acetic acid; wherein the distribution of the indicating layer provides for a visually noticeable color change against the background of the colored interior elastomeric layer upon a breach or contamination event by a selected chemical.

B. The breach or contamination indicating elastomeric article of Embodiment A, wherein the indicator layer is the solid particles sandwiched between the interior elastomeric layer and another elastomeric layer.

C. The breach or contamination indicating elastomeric article of Embodiment A or B, wherein the indicator layer is or comprises the solid particles suspended in a binder polymer.

D. A contamination indicating elastomeric article of one of Embodiments A to C, wherein any elastomeric layer exterior to the indicating layer is not a substantial resistant layer.

E. The contamination indicating elastomeric article of Embodiment D, wherein the indicator layer is the solid particles sandwiched between the interior elastomeric layer and another elastomeric layer.

F. The contamination indicating elastomeric article of Embodiment D, wherein the indicator layer is the solid particles adherent to an exterior surface of the interior elastomeric layer.

G. The contamination indicating elastomeric article of Embodiment D, wherein the indicator layer is or comprises the solid particles suspended in a binder polymer.

H. A breach indicating elastomeric article of one of Embodiments A to C, comprising an exterior elastomeric layer selected to be more resistant to permeation by the selected chemical(s) than the interior elastomeric layer, and to be sufficiently translucent to allow the function of the indicator layer.

I. The breach indicating elastomeric article of Embodiment H, wherein the indicator layer is the solid particles sandwiched between the interior elastomeric layer and another elastomeric layer.

J. The breach indicating elastomeric article of Embodiment H, wherein the indicator layer is or comprises the solid particles suspended in a binder polymer.

K. The breach indicating elastomeric article of Embodiment H, wherein the exterior layer and the interior layer each independently comprises a elastomer selected from the group consisting of carboxylated acrylonitrile butadiene, non-carboxylated acrylonitrile butadiene, polychloroprene, natural rubber, synthetic polyisoprene, polyurethane, and combinations thereof.

L. The breach indicating elastomeric article of Embodiment K, wherein one or more of the exterior elastomeric layer or the interior elastomeric layer has density consistent with aqueous latex dipping.

M. The breach or contamination indicating elastomeric article of one of Embodiments A to G, wherein the interior layer comprises a elastomer selected from the group consisting of carboxylated acrylonitrile butadiene, non-carboxylated acrylonitrile butadiene, polychloroprene, natural rubber, synthetic polyisoprene, polyurethane, and combinations thereof.

N. The breach or contamination indicating elastomeric article of Embodiment M, wherein the interior elastomeric layer has density consistent with aqueous latex dipping.

O. The breach or contamination indicating elastomeric article of one of Embodiments A to N, in the form of a glove.

P. A combination of a chemical protective article formed of laminated LCP multilayer film and the breach or contamination indicating elastomeric article of one of embodiments A to O, shaped and sized to fit to the interior of the laminated LCP multilayer film article.

Q. The combination of Embodiment P, wherein the two articles are bonded together.

R. A method of forming a breach or contamination indicating elastomeric article of one of Embodiments A to O, comprising: creating the interior elastomeric layer by aqueous dipping; and applying the indicator layer to the interior elastomeric layer.

S. A method of forming a breach indicating elastomeric article of one of Embodiments H to L, comprising: creating the interior elastomeric layer by aqueous dipping; creating the exterior elastomeric layer by aqueous dipping; and applying the indicator layer to the interior or exterior elastomeric layer prior to the creation on the indicator layer of the other elastomeric layer.

T. A method of forming a combination of a chemical protective article of Embodiment P, comprising inflating the breach or contamination indicating article to provide a close contact between the indicating article and the multilayer film; and bonding the indicating article and the multilayer film while they are in close contact.

U. A method of forming a combination of a chemical protective article of Embodiment P, comprising: inflating the breach or contamination indicating article to provide a close contact between the indicating article and the multilayer film; and bonding the indicating article and the multilayer film while they are in close contact.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A breach or contamination indicating elastomeric article for indicating a breach or contamination by a selected chemical or group of chemicals, the article having an exterior and interior and comprising:
   an interior elastomeric layer selected to resist permeation by the selected chemical(s), which interior layer is colored; and
   a contiguous or dis-contiguous indicating layer comprising dispersed solid particles of hydrophobic dye configured to provide enhanced color on contacting hexane, cyclohexane, xylene, ethyl ether, butyl acetate, methyl isobutyl ketone, methanol, acetonitrile and acetic acid, said solid form being a precipitate or crystalline form;
   wherein the distribution of the indicating layer is configured to provide a visually noticeable color change against the background of the colored interior elastomeric layer upon a breach or contamination event by a selected chemical, and wherein the solid particles are concentrated so as to reduce their color impact prior to breach or contamination indication by being in said solid form.

2. The breach or contamination indicating elastomeric article of claim 1, wherein the indicator layer is the solid particles sandwiched between the interior elastomeric layer and another elastomeric layer.

3. The breach or contamination indicating elastomeric article of claim 1, wherein the indicator layer comprises the solid particles suspended in a binder polymer.

4. A contamination indicating elastomeric article of claim 1, wherein any elastomeric layer exterior to the indicating layer is not a substantial resistant layer.

5. The contamination indicating elastomeric article of claim 4, wherein the indicator layer is the solid particles sandwiched between the interior elastomeric layer and another elastomeric layer.

6. The contamination indicating elastomeric article of claim 4, wherein the indicator layer is the solid particles adherent to an exterior surface of the interior elastomeric layer.

7. The contamination indicating elastomeric article of claim 4, wherein the indicator layer comprises the solid particles suspended in a binder polymer.

8. A breach indicating elastomeric article of claim 1, comprising:
   an exterior elastomeric layer selected to be more resistant to permeation by the selected chemical(s) than the interior elastomeric layer, and to be sufficiently translucent to allow the function of the indicator layer.

9. The breach indicating elastomeric article of claim 8, wherein the indicator layer is the solid particles sandwiched between the interior elastomeric layer and another elastomeric layer.

10. The breach indicating elastomeric article of claim 8, wherein the indicator layer comprises the solid particles suspended in a binder polymer.

11. The breach indicating elastomeric article of claim 8, wherein the exterior layer and the interior layer each independently comprises a elastomer selected from the group consisting of carboxylated acrylonitrile butadiene, non-carboxylated acrylonitrile butadiene, polychloroprene, natural rubber, synthetic polyisoprene, polyurethane, and combinations thereof.

12. The breach indicating elastomeric article of claim 11, wherein one or more of the exterior elastomeric layer or the interior elastomeric layer has density consistent with aqueous latex dipping.

13. The breach or contamination indicating elastomeric article of claim 1, wherein the interior layer comprises a elastomer selected from the group consisting of carboxylated acrylonitrile butadiene, non-carboxylated acrylonitrile butadiene, polychloroprene, natural rubber, synthetic polyisoprene, polyurethane, and combinations thereof.

14. The breach or contamination indicating elastomeric article of claim 13, wherein the interior elastomeric layer has density consistent with aqueous latex dipping.

15. The breach or contamination indicating elastomeric article of claim 1, in the form of a glove.

16. A combination of a chemical protective article formed of laminated liquid crystal polymer multilayer film and the breach or contamination indicating elastomeric article of claim 1, shaped and sized to fit to the interior of the laminated LCP multilayer film article.

17. The combination of claim 16, wherein the two articles are bonded together.

18. A method of forming a breach or contamination indicating elastomeric article of claim 1, comprising:
- creating the interior elastomeric layer by aqueous dipping; and
- applying the indicator layer to the interior elastomeric layer.

19. A method of forming a breach indicating elastomeric article of claim 8, comprising:
- creating the interior elastomeric layer by aqueous dipping;
- creating the exterior elastomeric layer by aqueous dipping; and
- applying the indicator layer to the interior or exterior elastomeric layer prior to the creation on the indicator layer of the other elastomeric layer.

20. A method of forming a combination of a chemical protective article of claim 16, comprising:
- inflating the breach or contamination indicating article to provide a close contact between the indicating article and the multilayer film; and
- bonding the indicating article and the multilayer film while they are in close contact.

21. The breach or contamination indicating elastomeric article of claim 1, wherein the solid particles have average particle size from about 0.5 microns to about 4 microns.

22. The breach or contamination indicating elastomeric article of claim 1, wherein the indicator layer is the solid particles sandwiched between the interior elastomeric layer and another elastomeric layer, wherein in manufacture the second applied of these two elastomeric layers is applied by aqueous dipping.

23. The breach indicating elastomeric article of claim 11, wherein the exterior elastomeric layer and the interior elastomeric layer have density consistent with aqueous latex dipping.

24. A breach or contamination indicating elastomeric article for indicating a breach or contamination by a selected chemical or group of chemicals, the article having an exterior and interior and comprising:
- an interior elastomeric layer, formed by aqueous dipping, selected to resist permeation by the selected chemical(s), which interior layer is colored;
- a contiguous or dis-contiguous indicating layer comprising dispersed solid particles of hydrophobic dye configured to provide enhanced color on contacting an organic solvent, said solid form being a precipitate or crystalline form; and
- an exterior elastomeric layer, formed by aqueous dipping, wherein the two elastomeric layers sandwich the indicating layer,
- wherein the distribution of the indicating layer is configured to provide a visually noticeable color change against the background of the colored interior elastomeric layer upon a breach or contamination event by a selected chemical, and wherein the solid particles are concentrated so as to reduce their color impact prior to breach or contamination indication by being in said solid form.

25. The breach or contamination indicating elastomeric article of claim 24, in the form of a glove.

26. The breach indicating elastomeric glove of claim 25, wherein the exterior elastomeric layer is selected to be more resistant to permeation by organic solvents than the interior elastomeric layer, and to be sufficiently translucent to allow the function of the indicator layer.

* * * * *